United States Patent
Cowan, Jr. et al.

(10) Patent No.: US 6,585,677 B2
(45) Date of Patent: Jul. 1, 2003

(54) SHUNT

(76) Inventors: John A. Cowan, Jr., 370 Village Green, Apt. 104, Ann Arbor, MI (US) 48105; Kieran Murphy, 119 Beechdale Rd., Baltimore, MD (US) 21210; Michael Williams, 1394 Rivermist Ct., Baltimore, MD (US) 21226; Daniele Rigamonti, 2807 Old Court Rd., Baltimore, MD (US) 21208

( * ) Notice: Subject to any disclaimer, the term of this patent is extended or adjusted under 35 U.S.C. 154(b) by 0 days.

(21) Appl. No.: 09/942,223

(22) Filed: Aug. 29, 2001

(65) Prior Publication Data

US 2002/0026138 A1 Feb. 28, 2002

Related U.S. Application Data

(60) Provisional application No. 60/228,937, filed on Aug. 30, 2000.

(51) Int. Cl.$^7$ ............................................ A61M 5/00
(52) U.S. Cl. .................... 604/9; 604/10; 604/8
(58) Field of Search .................. 604/8–10, 523, 604/264, 65, 9; 600/561, 300

(56) References Cited

U.S. PATENT DOCUMENTS

| | | | |
|---|---|---|---|
| 4,598,579 A | * | 7/1986 | Cummings et al. ............ 604/9 |
| 4,632,668 A | * | 12/1986 | Wilson et al. ............... 604/540 |
| 5,766,195 A | | 6/1998 | Nobles |
| 5,795,307 A | | 8/1998 | Krueger |
| 5,902,283 A | | 5/1999 | Darouiche et al. |
| 5,924,424 A | * | 7/1999 | Stevens et al. ............. 128/898 |
| 6,050,969 A | | 4/2000 | Kraus |
| 6,083,174 A | | 7/2000 | Brehmeier-Flick |
| 6,090,062 A | * | 7/2000 | Sood et al. ................. 604/133 |
| 6,126,628 A | | 10/2000 | Nissels |
| 6,132,415 A | * | 10/2000 | Finch et al. ........... 604/288.01 |
| 6,162,487 A | | 12/2000 | Darouiche |
| 6,168,801 B1 | | 1/2001 | Heil, Jr. et al. |
| 6,201,980 B1 | | 3/2001 | Darrow et al. |
| 6,248,080 B1 | * | 6/2001 | Miesel et al. ................ 600/311 |
| 6,264,625 B1 | | 7/2001 | Rubenstein et al. |
| 6,383,160 B1 | * | 5/2002 | Madsen ....................... 604/10 |

OTHER PUBLICATIONS

"Review of Medical Physiology", William F. Fanong, MD, 1987.
Drake et al, The Shunt Book, 1995, Chapter 4, pp 71–119; Table of Contents; Blackwell Science, Ann Arbor, MI, USA.
Rein Precht et al, The Medos Hakim Programmable Value in the Treatment of pediatric Hydrocephalus, Child's Nerv Syst (1997) 13:588–594, 1997.
Miyake et al, A New Ventriculoperitoneal Shunt with A Telemetric Intracranial Pressure Sensor: . . . , Neurosurgery, vol. 40, No. 5, May 1997.

* cited by examiner

Primary Examiner—Angela D. Sykes
Assistant Examiner—Leslie R Deak
(74) Attorney, Agent, or Firm—Katten Muchin Zavis Rosenman

(57) ABSTRACT

A shunt for draining cerebral spinal fluid from the brain is provided. In an embodiment, the shunt includes a master control unit that is located in the abdomen, which interconnects a ventricular catheter and a second catheter, typically located in the peritoneal cavity. In a specific embodiment, the master control unit includes a variety of 'smart' features including at least one access port to allow the injection of solutions for the prevention or removal of blockages in the catheter, and/or antibiotics. The access port can have other uses, such as allowing a point of access for physical navigation of a catheter or the like within the shunt, thereby providing another option for breaking-up blockages, and/or allowing an access point for repairing the shunt's components. Additionally, the master control unit includes a diagnostic unit that transmits, either wirelessly or through a wired connection via the access port, diagnostic information about the status of the patient and/or the shunt.

44 Claims, 2 Drawing Sheets

SHUNT

PRIORITY Claim

The present application claims priority from U.S. Provisional Patent Application No. 60/228,937 and filed Aug. 30, 2000, the contents of which are incorporated herein by reference.

FIELD OF THE INVENTION

The present invention relates generally to apparatuses for the treatment of hydrocephalus or the like, and more particularly relates to cerebrospinal fluid ("CSF") shunts.

BACKGROUND OF THE INVENTION

CSF shunts are well known and used broadly to treat patients with chronic hydrocephalus. In simple terms, such shunts typically have an inlet located in the patient's brain, and an outlet into some portion of the body which can accept and expel the excess fluid. A detailed discussion of prior art CSF shunts can be found in Drake et al, *The Shunt Book*, ©1995 Blackwell Science, Inc. Massachusetts, ("Drake") the contents of which are incorporated herein by reference.

More particularly, ventriculoperitoneal ("VP") shunts are designed to drain CSF from the brain into the peritoneal cavity. VP shunts are used in a variety of medical conditions and are implanted in both young and old patients. Certain configurations of prior art VP shunts can include a ventricular catheter, a flow-valve that can be changed by an external magnet, and a tunneled abdominal catheter. Further discussion on this type of shunt can be found in Reinprecht A., et al., "The Medos Hakim programmable valve in the treatment of pediatric hydrocephalus.", *Childs Nerv Syst*, 1997 November–December; 13(11–12):588–93. The ventricular cather and flow-valve are inserted through a scalp incision. The major complications from these and other prior art shunts include infection, obstruction, disconnection, under draining, and over draining, all of which can lead to serious injury and even death. The symptoms of shunt failure and malfunction are nonspecific and include fever, nausea, vomiting, irritability and malaise. A patient presenting to a medical facility with such symptoms warrants a thorough radiological, laboratory, and occasionally a surgical evaluation. As known to those of skill in the art, insertion of CSF shunts requires a highly skilled surgeon or radiologist working under CT X-Ray guidance, but once inserted, such shunts are frequently prone to failure.

More recent shunts that attempt to overcome some disadvantages of older shunts include the use of telemetry, as discussed in Miyake H. et al., "A new ventriculpertoneal shunt with a telemetric intracranial pressure sensor: clinical experience in 94 patients with hydrocephalus", *Neurosurgery*, 1997 May; 40(5): 931–5 and Munshi H., "Intraventricular pressure dynamics in patients with ventriculopleural shunts: a telemetric study", *Pedatr Neursurg*, 1998 February; 28(2): 67–9 Despite the fact that Miyake and Munshi teach the use of telemetrics with shunts, the shunts taught therein are still prone to failure due to infection, blockages and other difficulties, such that failures of such shunts can still require complete replacement of the shunt.

SUMMARY OF THE INVENTION

It is therefore an object of the present invention to provide a CSF shunt that obviates or mitigates at least one of the disadvantages of the prior art.

In an aspect of the invention, there is provided a shunt for draining cerebral spinal fluid comprising a first catheter for insertion into an area of the patient that has excess CSF, and for receiving CSF therefrom. The shunt also includes a second catheter for insertion into a drainage cavity for draining the CSF, and a master control unit for insertion into the patient in a biocompatible location. The master control unit interconnects the catheters via a catheter line, and has a regulator for selectively draining an excess of the CSF. The shunt also includes at least one access port intermediate the first catheter and the second catheter, and which is placed subcutaneously such that when the access port is inserted into the patient, the access port provides a point of access to the shunt for allowing a treatment a condition associated with the shunt without requiring the shunt's removal.

In a particular implementation of the first aspect, the CSF space is a ventricle.

In a particular implementation of the first aspect, the drainage space is one of the patient's peritoneum, pleural space or vascular space.

In a particular implementation of the first aspect, the biocompatible location is one of the patient's skull, chest cavity or abdomen.

In a particular implementation of the first aspect, the regulator is a mechanical flow-valve regulator.

In a particular implementation of the first aspect, the regulator is a microprocessor based valve-gauge assembly for determining when the CSF requires draining and allowing the CSF to drain from the ventricle to the drainage cavity.

In a particular implementation of the first aspect, the microprocessor based valve-gauge assembly has a normally-open position to allow a preset amount of drainage of CSF in the event of a power-failure to valve-gauge assembly.

In a particular implementation of the first aspect, the shunt further comprises a diagnostic unit for detecting abnormal metabolic activity within the patient, and a transmitter for delivering the activity to a receiver external to the patient.

In a particular implementation of the first aspect, the transmitter is operable to perform the delivery wirelessly to the receiver.

In a particular implementation of the first aspect, the transmitter includes a memory buffer for accumulating data from the diagnostic unit prior to the delivery, In a particular implementation of the first aspect, the condition is a blockage and the at least one access port allows an introduction point of introduction of a blockage-ablation device within the catheter line for physically breaking-up the blockage.

In a particular implementation of the first aspect, the blockage-ablation device is a micro-catheter with a tip suitable for piercing the blockage.

In a particular implementation of the first aspect, blockage-ablation device is a radio-frequency ablation device.

In a particular implementation of the first aspect, the at least one access ports is mounted on an exterior of the master control, the control unit further having a fluid bladder accessible via the access port for injection of at least one solution for treatment of a condition.

In a particular implementation of the first aspect, condition a blockage and a solution for treatment thereof and injection via the access port is an anticoagulant or a thrombolytic.

In a particular implementation of the first aspect, the condition is an infection and a solution for treatment thereof and injection via the access port is an antibiotic.

In a particular implementation of the first aspect, the at least one access port includes a self-healing plastic membrane.

In a particular implementation of the first aspect, there at least two access ports and wherein one of the access ports is located on the catheter line intermediate the master control unit and the second catheter and wherein a second one of the access ports is located on the catheter line intermediate the first catheter and the master control unit.

In a particular implementation of the first aspect, the shunt further comprises a transmitter connected to the valve-gauge assembly for gathering pressure information therefrom, the transmitter for reporting the pressure information to a receiver external to the patient.

In a particular implementation of the first aspect, at least a portion of the shunt has an antibiotic coating.

A shunt for draining cerebral spinal fluid from the brain is provided. In an embodiment, the shunt includes a master control unit that is located in the abdomen, chest wall, in the skull, on the skull or other suitable location, which interconnects a first catheter and a second catheter that is typically located in the peritoneal cavity. In a specific embodiment, the master control unit is located in the abdomen, and includes a variety of intelligent features including at least one access port to allow the injection of solutions for the prevention or removal of blockages in the catheter, and/or antibiotics. Additionally, such ports can allow a radiologist (or the like) to navigate within the shunt to physically remove blockages or perform other remedial and/or diagnostic activities throughout the shunt system. Additionally, the master control unit includes a diagnostic unit that transmits, either wirelessly or through a wired connection via the access port, diagnostic information about the status of the patient and/or the shunt.

BRIEF DESCRIPTION OF THE DRAWINGS

Preferred embodiments of the invention will now be discussed, by way of example only, with reference to the attached Figures, in which.

DETAILED DESCRIPTION OF THE INVENTION

Figure 1:
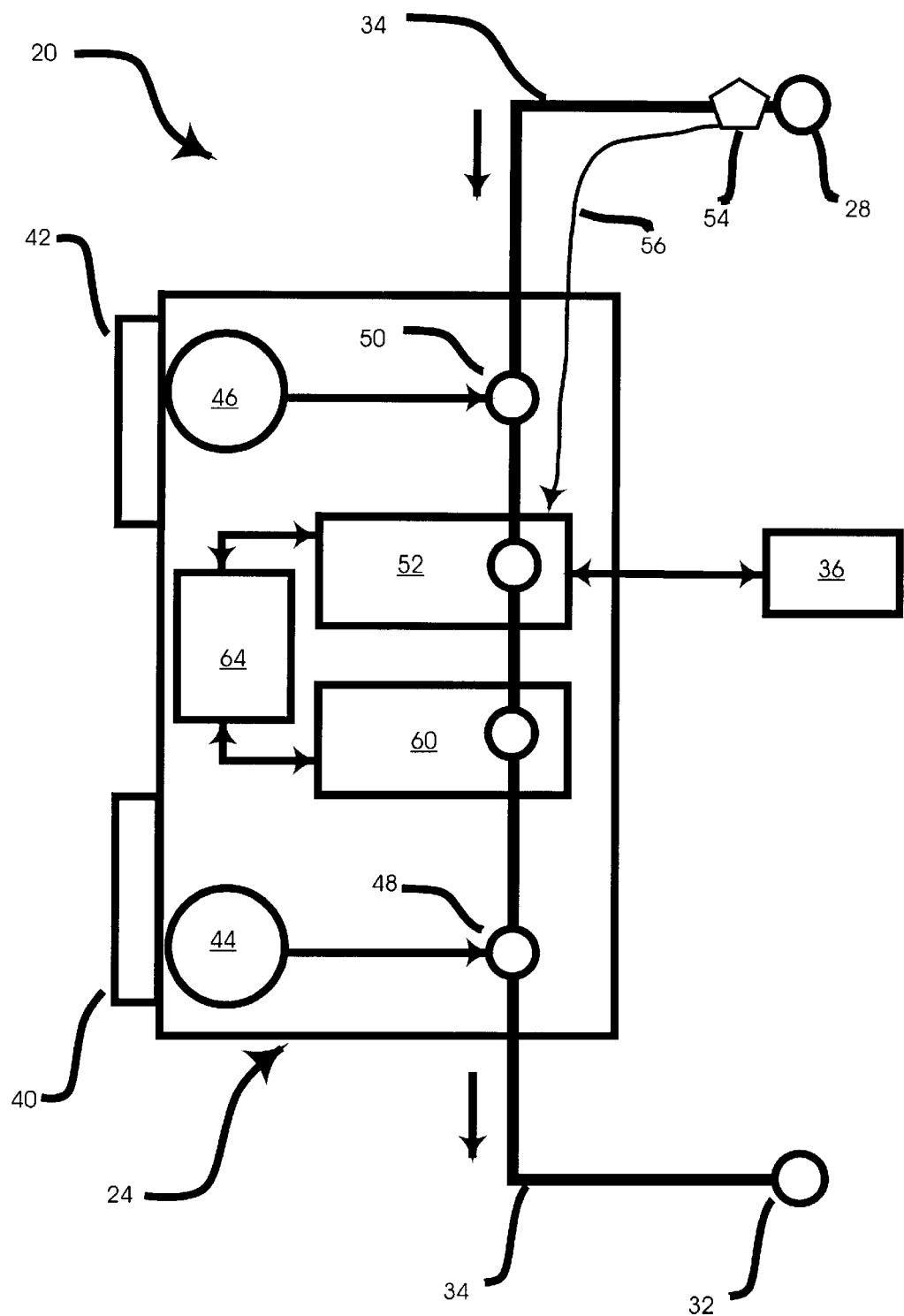
FIG. 1 is a schematic representation of a CSF shunt in accordance with an embodiment of the invention; and, FIG. 2 is a schematic representation of a CSF shunt in accordance with another embodiment of the invention.

Referring now to FIG. 1, a schematic representation of a CSF shunt is indicated generally at 20. Shunt 20 comprises a master control unit 24 (which can also be referred to as the active component) that interconnects a first catheter 28, and a second catheter 32 via a catheter line 34. Master control unit 24 is preferably minitiarized and made of a biocompatible material such that it can be safely inserted in the patient's abdomen, either intra-peritoneal or extra-peritoneal, using a standard abdominal incision, and remain therein as needed to drain CSF.

After master control unit 24 is inserted into the patient's abdomen, first catheter 28 can then be tunneled from the abdomen rostrally (or caudaly) into a CSF space in the scalp to serve as an inlet for excess CSF, which in a present embodiment is a ventricle. (As used herein, the term CSF space includes any space in the body that can generate an excess of CSF requiring drainage.) A small incision in the scalp can then be used to assist in the final positioning of first catheter 28 within the patient's head. By tunneling into the scalp, it is contemplated that this can obviate the need to separately connect catheter 28 to control unit 24.

Similarly, second catheter 32 can be tunneled from below, up into the peritoneal cavity to serve as an outlet for the CSF. The tip of second catheter 32 is chosen to increase the flow of CSF drainage, and to reduce the likelihood of obstruction thereat. In one embodiment, the tip of catheter 32 is static, having a conical shape with drainage ports along the surface and underside thereof. In another embodiment, the tip of catheter 32 is resiliently expandable, for breaking up debris, adhesions or other occlusions that can develop over time. A suitable expandable tip is an appropriately modified angioplasty balloon, which can be inflated to break up adhesions.

Master control unit 24 is powered by a battery 36 (or other self-contained power source), such as a high-capacity battery such as already widely used in pacemakers, stimulators, defibrillators and the like. It is presently preferred that battery 36 be located external to master control unit 24 and inserted in subcutaneous tissue to provide easy access for replacement in the event of failure. It is also contemplated, however, that battery 36 could be integrally housed within master control unit 24.

Master control unit 24 is also characterized by a first access port 40 and a second access port 42, which provide access to certain other components within shunt 20, the details of which will be discussed in greater detail below. Thus, as master control unit 24 is inserted in the abdomen, is it also oriented within the patient subcutaneously, such that access ports 40 and 42 are readily accessible. Further, the placement of master control 24 is preferably particularly chosen to reduce the likelihood of rotation or other movement of master control unit 24, to reduce the likelihood that ports 40 and 42 become inaccessible due to rotation or shifting in the patient over time.

Access ports 40 and 42 include a self-healing plastic membrane, which can be punctured with a sharp instrument (i.e. a needle, catheter, or the like) and then reseal seal itself upon withdrawal the instrument. Such self-healing plastic membranes can be adapted from currently available membranes used in vascular access devices and other applications requiring puncturing and resealing.

Master control unit 24 houses a first fluid bladder 44 proximal to first access port 40, and a second fluid bladder 46 proximal to second access port 42. Thus, when access port 40 or 42 is opened, the bladder 44 or 46 respective thereto, is accessible for filling via injection or for providing other access to shunt 20. Bladders 44 and 46 are typically made of silicon or other biocompatible material. Such injections could include heparin (or some other anti-thrombotic or anti-collagen agent) and/or an antibiotic solution, such as for prophylaxis treatment or treatment of infection. Bladders 44, 46 are connected to catheter line 34 within control unit 24, via a one-way valve 48, 50 respectively. Thus, for example, an injection into bladder 44 can eventually work its way into catheter line 34 (particularly the portion between control unit 24 and the second catheter 32) and thereby dissolve any blockages therein, without the need for more invasive surgery required to replace the entire shunt 24. Alternatively, an injection may be desired to be eventually introduced into the patient, and using bladder 44 such an injection can be eventually introduced into the patient's peritoneal cavity. It will be understood by those of skill in the art that the size of bladder 44, and the mechanical flow characteristics of valves 48 are chosen to allow an appropriate quantity and rate of delivery of the injection into line 34. By the same token, access port 42, bladder 46 and valve 50 can also provide access to shunt 20, and in particular to the portion of shunt 20 between master control unit 24 and first catheter 28, and in turn, the patient's skull. In other embodiments, it is contemplated that additional access ports, bladders and valves could be provided in order to provide additional means to introduce injections into shunt 20 and/or the patient in a manner with reduced intrusion to the patient. Where a patient is indicated for other injection therapies, such as chemotherapy, the present invention thus has the added benefit of providing means for introducing such injections without the need for vascular access devices.

Also housed within master control unit 24 is a microprocessor-based valve-gauge assembly 52. Valve-gauge assembly 52 includes known components, including a pressure gauge for monitoring the pressure of CSF present in line 34, and a valve for selectively allowing CSF to flow through line 34 and towards second catheter 32. Valve-gauge assembly 52 also includes a ventricular-gauge 54 that is located proximal to ventricular-catheter 28 and connected to the portion of assembly 52 housed within master control unit 24 via a control line 56, which is preferably inserted into the patient in conjunction with first catheter 28. Accordingly, in certain configurations control line 56 can be physically connected in parallel to the portion of catheter line 34 that runs between first catheter 28 and master control unit 24, thereby allowing control line 56 and that portion of catheter line 34 to be inserted simultaneously.

Valve-gauge assembly 52 further includes a microprocessor (or other processing means) that is operable to receive inputs from the pressure gauges associated with assembly 52 and to output control signals to the valve within assembly 52. The microprocessor is programmed with various criteria that determine when the valve should be opened or closed. Any decision-making criteria that determines the appropriate and/or desired drainage of CSF from the ventricles (or other CSF space) to the peritoneal cavity (or other drainage space) can be used. For example, such decision making criteria could be based on different times of day. Additionally, valve-gauge assembly 52 could also be provided with an accelerometer or other movement sensor, and/or a mercury switch or other type of position sensor that provides additional feedback as to the movement and/or position of the patient. Such information can be included with the information provided by the pressure gauges of assembly 52, as part of the decision making critera as to how much CSF drainage to allow. One known valve-assembly 52 that could be extended beyond its current functionality to incorporate the additional functionality described hereabove (and thereby provide a novel shunt over the prior art) is taught in Reinprecht, previously cited.

It is also presently preferred that the valve portion of valve-gauge assembly 52 be configured to be normally-open to provide a pre-set rate of flow of CSF in the event of a power failure of battery 36.

Master control unit 24 additionally houses a diagnostic unit 60, that includes a probe operable to sample CSF passing through line 34, and the outer surface of line 34 to detect the presence abnormal metabolic activity within the patient. Diagnostic unit 60 can be based on any means for detecting such abnormal metabolic activity, such as a ph/Redox. Diagnostic unit 60 further includes a microprocessor for interpreting the data gathered by the probe, and, based on a predefined set of diagnostic criteria, make determinations as to whether shunt 20 is operating properly. Such diagnostic criteria would include, for example, whether the pH level of CSF flowing through unit 60 changes by a predetermined amount, thereby indicating the presence of infection.

The processing units of valve-gauge assembly 52 and diagnostic unit 60 are both connected to a transmitter 64. Transmitter 64 is operable to receive information from valve-gauge assembly 52 and diagnostic unit 60 and emit that information to a computing device external to the patient. In a present embodiment, transmitter 64 operates wirelessly, emitting an RF signal detectable by a receiver located proximal to the patient. In order to reduce battery consumption, it is preferred that transmitter 64 emit at a low power level. The external computing device that receives the emitted signal can then use the information to either automatically to diagnose any malfunction or infection, and/or simply pass the data in human-readable format to the patient's doctor or other skilled professional for review and analysis.

Figure 2:
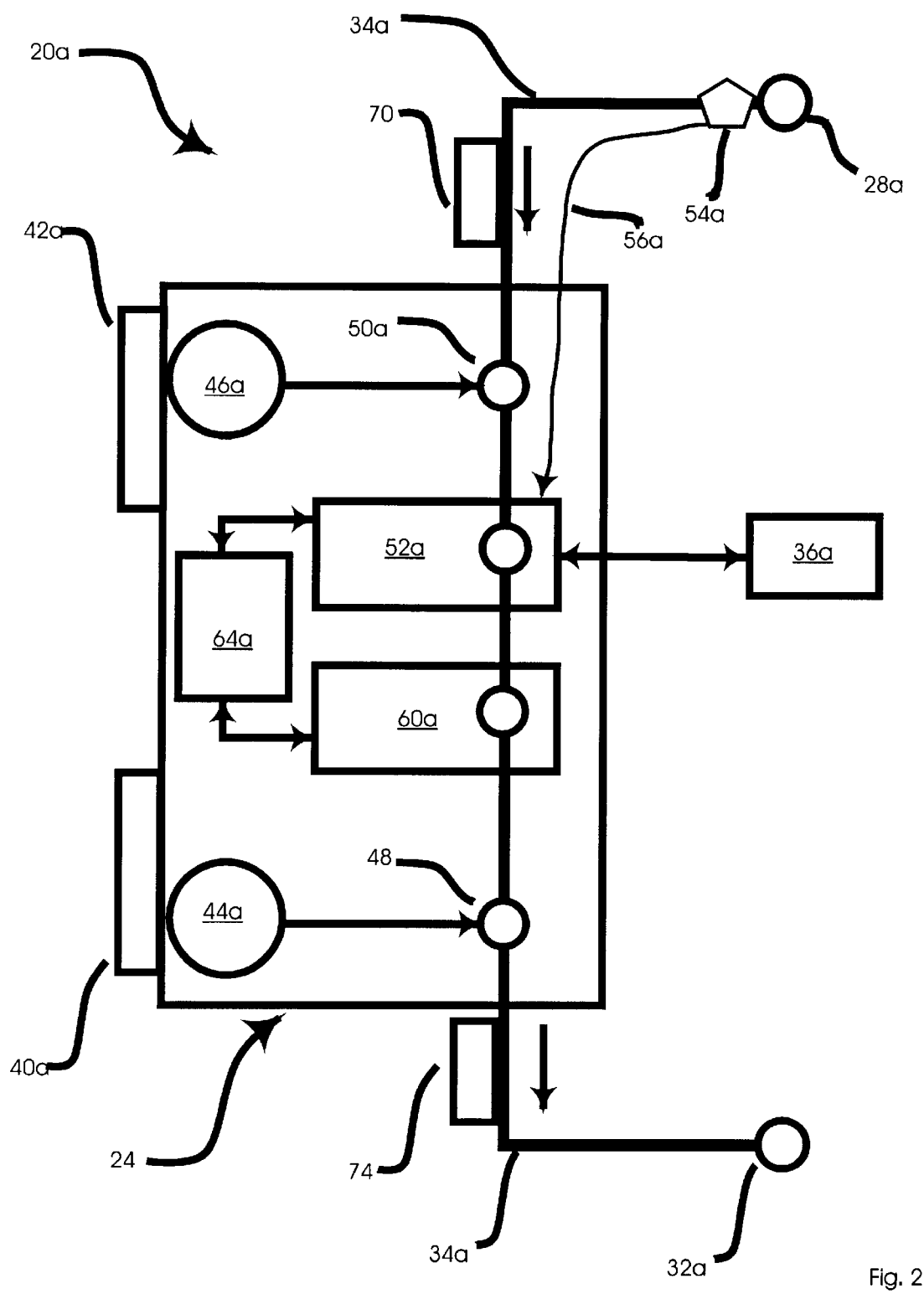

Referring now to FIG. 2, in another embodiment of the invention there is provided a shunt 20a. Like components in shunt 20a of FIG. 2 to the components of shunt 20 of FIG. 1 are given like reference numbers, followed by the suffix "a". Thus, the components and operation of shunt 20b are substantially identical to the components of shunt 20, except that in shunt 20a two additional access ports 70 and 74 are provided. Access port 70 is located along catheter line 34a intermediate first catheter 28 and master control unit 24, while access port 74 is located along catheter line 34a at a point intermediate master control unit 24 and second catheter 32. Access ports 70 and 74 are thus characterized by a chamber with an opening oriented towards the periphery of the patient's body, and covered with a self-healing plastic membrane, such as that previously described for access ports 40, 42.

Thus, access ports 70 and 74 provide additional points for injection, similar to access ports 40 and 42. Access ports 70 and 74 also provide a means for a radiologist (or the like) to use X-ray guidance in order to physically navigate items such as catheters, wires, radio-frequency blockage ablation devices, imaging devices based on fiber optics or ultra sound, within the various passageways of catheter line 34 and other components of shunt 20a. In this manner, blockages within catheter line 34 can by physically broken up using a catheter to tunnel through such blockages within line 34. Other uses for navigation within catheter line 34 will occur to those of skill in the art.

Shunt 20 can be placed in patient using traditional surgical techniques, or it can be placed using an image-guidance technique such as radiological, CT, MR, fluoroscopy, or the like. Additionally, each component of shunt 20 can be coated with, or made from a material that allows such component to be readily viewed using a complementary imaging system. For example, such components could be radio-opaque for viewing under X-ray.

While only specific combinations of the various features and components of the present invention have been discussed herein, it will be apparent to those of skill in the art that desired subsets of the disclosed features and components and/or alternative combinations of these features and components can be utilized, as desired. For example, the embodiments discussed herein refer to a fluid bladder, it will be understood that other means for injecting a solution can be provided.

Furthermore, while the embodiments discussed herein contemplate the placement of master control unit 24 in the abdomen, it is contemplated that master control unit 24 can be modified for placement in other suitable areas intermediate first catheter 28 and second catheter 32, such as the chest wall (similar to a pacemaker) or in the skull.

It is also to be understood that the access ports 40, 42 of FIG. 1 can also be used for physically accessing shunt 20 for repairing master control unit 24, or for introducing a microcatheter or the like, in addition to using such ports 40, 42 for injections.

In addition, while not a requirement it is presently preferred that all or part of the components of shunt 24 are made from infection-resistant materials, such as using silicon tubing coated/impregnated with an antibiotic for catheter line 34.

It is also contemplated that all or part of the various components of shunt 24 can be covered with an adhesion resistant coating.

While it is presently preferred to include microprocessor-based valve gauge assembly 52, it is contemplated that in other embodiments of the invention such an assembly 52 could be replaced with another type of regulator, such as a traditional mechanical flow-valve currently found in CSF shunts, and thereby still provide an advantageous and novel shunt having access ports that can be used to treat conditions affecting the patient, such as those typically associated with the shunt's failure or infection of the patient, or the like.

While the embodiments herein teach the locating of first catheter 28 in the ventricles, it will now be apparent to those of skill in the art other types of receiving catheters for receiving excess CSF depending on the location from which the CSF is to be drained.

In addition, while the embodiments herein discuss the use of one-way valve 48 in conjunction with bladders 44 and 46, in other embodiments it can be desired to incorporate different types of valves in order to allow aspiration, in addition to or in lieu of injection. For example, it can be desired to have one way valves 48 and 50 shown in FIG. 1 replaced with two-way valves, and include a one-way way valve on the portion of catheter line 34 intermediate master control unit 24 and second catheter 32 in order to ensure that fluids only flow from master control unit 24 towards second catheter 32—thereby freeing up ports 40 and 42 for use as aspiration ports.

It is also contemplated that transmitter 64 can be substituted for a transceiver, that would not only permit downloading of data from shunt 20 to an external computing device, but would also accept uploaded information to shunt 20 from an external computing device. Such uploaded information can include, for example, reprogramming instructions for software programming used in the operation of in valve-gauge assembly 52 and/or diagnostic unit 60.

Furthermore, while the embodiments discussed herein refer to two access ports with associated bladders and other means to access catheter line 34, in other embodiments it is contemplated that there may be only one access port, or more than two access ports, as desired. Furthermore, it is contemplated that such additional or fewer access ports could also be provided with additional bladders per access port, as desired.

Furthermore, while transmitter 64 of the embodiments discussed herein is wireless, it is also contemplated that transmitter 64 could function wirelessly, by attaching a data port, such as a serial port to transmitter 64, that is accessible via port 40. Further, it is also contemplated that transmitter 64 can include a memory buffer to allow an accumulation of data to be gathered, prior to downloading the data by transmission, and thereby providing a greater sampling of data without the need for interfering with the patient's mobility and/or relying on the patient's full-time proximity to a receiver to detect the transmission.

The present invention provides a novel shunt for draining CSF that has a main control unit that is located in the abdomen of the patient. The main control unit includes an access port that allows the injection of a solution into the shunt. Such a solution can include an anticoagulant or collagenase to treat an obstruction in the catheter. Other solutions can be injected, as desired. By providing one, two or more access ports, problems with the shunt can be addressed without the need for invasive surgery, such as removing and/or replacing the shunt. The access ports can also be used to allow physical navigation within the passageways of the shunt, thereby allowing repair of the shunt under radiological guidance, or to allow blockages to be broken-up under radiological guidance. Additionally, diagnostic functions are included within the shunt to provide information as to the operation of the shunt and/or information about the pressures and rates of drainage of CSF in the patient. Such diagnosis can also mitigate the need for invasive surgery, as can be required in certain prior art shunts, to ascertain the cause of a shunt failure. The shunt of the present invention can thus allow the diagnosis of shunt failure, and treatment thereof, without the need for additional surgery on the patient.

What is claimed is:

1. A cerebral spinal fluid (CSF) draining shunt, comprising:
    a CSF space catheter configured to (i) be inserted into a CSF space of a patient, and (ii) to receive CSF from the CSF space of the patient;
    a body cavity catheter configured to (i) be inserted into a body cavity of the patient, and (ii) to drain the CSF received by said CSF space catheter into the body cavity;
    an implantable master control unit configured to be implanted into the patient in a biocompatible location, said master control unit interconnecting said CSF space catheter and said body cavity catheter, said master control unit having a regulator for selectively draining an excess of said CSF from said CSF space catheter to said body cavity catheter; and
    at least one master control unit access port disposed in said master control unit intermediate said CSF space catheter and said body cavity catheter, said at least one master control unit access port being configured to provide access for remedial structure into said master control unit without requiring said master control unit's removal from the patient.

2. The shunt according to claim 1 wherein the CSF space comprises a ventricle.

3. The shunt according to claim 2 wherein the body cavity comprises at least one of the patient's peritoneum, pleural space, or vascular space.

4. The shunt according to claim 2 wherein said regulator comprises a microprocessor based valve-gauge assembly for (i) determining when said CSF requires draining and (ii) allowing said CSF to drain from said ventricle to said body cavity.

5. The shunt according to claim 4 wherein said microprocessor based valve-gauge assembly has a normally-open position to allow a preset amount of drainage of CSF in the event of a power-failure to said valve-gauge assembly.

6. The shunt according to claim 4 wherein said shunt further comprises a transmitter connected to said valve-gauge assembly for gathering pressure information therefrom, said transmitter for reporting said pressure information to a receiver external to said patient.

7. The shunt according to claim 1 wherein said biocompatible location is one of said patient's skull, chest cavity or abdomen.

8. The shunt according to claim 1 wherein said regulator comprises a mechanical flow-valve regulator.

9. The shunt according to claim 1 further comprising a diagnostic unit for detecting abnormal metabolic activity within said patient, and a transmitter for providing a delivery of said metabolic activity to a receiver external to said patient.

10. The shunt according to claim 9 wherein said transmitter is operable to perform said delivery wirelessly to said receiver.

11. The shunt according to claim 8 wherein said transmitter includes a memory buffer for accumulating data from said diagnostic unit prior to said delivery.

12. The shunt according to claim 1 further comprising a blockage-ablation device, and wherein said at least one access port is configured to allow an introduction of said blockage-ablation device into said master control unit.

13. The shunt according to claim 11 wherein said blockage-ablation device comprises a micro-catheter having a tip suitable for piercing said blockage.

14. The shunt according to claim 12 wherein said blockage-ablation device comprises a radio-frequency ablation device.

15. The shunt according to claim 12 wherein master control unit further comprises a fluid bladder accessible via said at least one access port, said fluid bladder being configured for injection therein of at least one solution.

16. The shunt according to claim 15 wherein said fluid bladder is configured for injection therein of an anticoagulant.

17. The shunt according to claim 15 wherein said fluid bladder is configured for injection therein of an antibiotic.

18. The shunt according to claim 1 wherein said at least one access port includes a self-healing plastic membrane.

19. The shunt according to claim 1 wherein said master control unit further comprises a control unit catheter line disposed between said CSF space catheter and said body cavity catheter, wherein said at least one access port comprises at least two access ports in said master control unit, wherein one of said access ports is located on said control unit catheter line intermediate said master control unit and said body cavity catheter, and wherein a second one of said access ports is located on said control unit catheter line intermediate said CSF space catheter and said master control unit.

20. The shunt according to claim 1 wherein at least a portion of said shunt has an antibiotic coating.

21. A CSF draining shunt according to claim 1, wherein said at least one master control unit access port is disposed upstream of said regulator.

22. A CSF draining shunt according to claim 21, further comprising another master control unit access port disposed downstream of said regulator.

23. A CSF draining shunt according to claim 22, further comprising a CSF space catheter access port disposed in said CSF space catheter.

24. A CSF draining shunt according to claim 23, further comprising a body cavity catheter access port disposed in said body cavity catheter.

25. A CSF draining shunt according to claim 24, wherein said regulator monitors a pressure of CSF in said CSF space catheter.

26. A CSF draining shunt according to claim 1, further comprising a body cavity catheter tip disposed at an end of said body cavity catheter, and wherein said body cavity catheter tip is expandable.

27. A CSF draining shunt according to claim 1, wherein said implantable master control unit is configured to be implanted into a chest of the patient.

28. A CSF draining shunt according to claim 1, wherein at least a portion of said body cavity catheter comprises an adhesion resistant material.

29. A CSF draining shunt according to claim 1, wherein at least a portion of said CSF space catheter comprises an infection resistant material.

30. A cerebral spinal fluid (CSF) draining shunt, comprising:
- a CSF space catheter configured to (i) be inserted into a CSF space of a patient, and (ii) to receive CSF from the CSF space of the patient;
- a body cavity catheter configured to (i) be inserted into a body cavity of the patient, and (ii) to drain the CSF received by said CSF space catheter into the body cavity;
- an implantable master control unit configured to be implanted into the patient in a biocompatible location, said master control unit interconnecting said CSF space catheter and said body cavity catheter, said master control unit having a regulator for selectively draining an excess of said CSF from said CSF space catheter to said body cavity catheter;
- a first access port disposed in said CSF space catheter and configured to provide access to the CSF space; and
- a second access port disposed in said body cavity catheter and configured to provide access to the body cavity.

31. A CSF draining shunt according to claim 30, further comprising at least one master control unit access port disposed in said master control unit intermediate said CSF space catheter and said body cavity catheter, said at least one master control unit access port being configured to provide access for remedial structure into said master control unit without requiring said master control unit's removal from the patient.

32. A CSF draining shunt according to claim 31, wherein said at least one master control unit access port is disposed upstream of said regulator.

33. A CSF draining shunt according to claim 32, further comprising another master control unit access port disposed downstream of said regulator.

34. A CSF draining shunt according to claim 33, wherein said implantable master control unit is configured to be implanted into a chest of the patient.

35. A CSF draining shunt according to claim 30, wherein at least a portion of said body cavity catheter comprises an adhesion resistant material.

36. A CSF draining shunt according to claim 35, wherein at least a portion of said CSF space catheter comprises an infection resistant material.

37. A cerebral spinal fluid (CSF) draining shunt, comprising:
- a CSF space catheter configured to (i) be inserted into a CSF space of a patient, and (ii) to receive CSF from the CSF space of the patient, said CSF space catheter comprising an adhesion resistant coating;
- a body cavity catheter configured to (i) be inserted into a body cavity of the patient, and (ii) to drain the CSF received by said CSF space catheter into the body cavity; and
- an implantable master control unit configured to be implanted into the patient in a biocompatible location, said master control unit interconnecting said CSF space catheter and said body cavity catheter, said master control unit having a regulator for selectively draining an excess of said CSF from said CSF space catheter to said body cavity catheter.

38. A CSF draining shunt according to claim 37, wherein at least a portion of said CSF space catheter comprises an infection resistant material.

39. A CSF draining shunt according to claim 37, further comprising at least one master control unit access port disposed in said master control unit intermediate said CSF space catheter and said body cavity catheter, said at least one master control unit access port being configured to provide access for remedial structure into said master control unit without requiring said master control unit's removal from the patient.

40. A CSF draining shunt according to claim 37, wherein said at least one master control unit access port is disposed upstream of said regulator.

41. A CSF draining shunt according to claim 40, further comprising another master control unit access port disposed downstream of said regulator.

42. A CSF draining shunt according to claim 37, wherein said implantable master control unit is configured to be implanted into a chest of the patient.

43. A CSF draining shunt according to claim 37, further comprising a CSF space catheter access port disposed in said CSF space catheter.

44. A CSF draining shunt according to claim 37, further comprising a body cavity catheter access port disposed in said body cavity catheter.

* * * * *